United States Patent
Kaneyama et al.

(10) Patent No.: US 6,778,944 B2
(45) Date of Patent: Aug. 17, 2004

(54) METHOD AND SYSTEM FOR MANAGING DATA

(75) Inventors: Miyuki Kaneyama, Tokyo (JP); Masumi Katagami, Tokyo (JP); Iwao Sakai, Tokyo (JP)

(73) Assignees: Jeol Ltd., Tokyo (JP); Jeol Engineering Co., Ltd., Tokyo (JP)

( * ) Notice: Subject to any disclaimer, the term of this patent is extended or adjusted under 35 U.S.C. 154(b) by 0 days.

(21) Appl. No.: 10/236,077

(22) Filed: Sep. 5, 2002

(65) Prior Publication Data

US 2003/0110010 A1 Jun. 12, 2003

(30) Foreign Application Priority Data

Sep. 10, 2001 (JP) ........................................ 2001-273105
Jul. 17, 2002 (JP) ........................................ 2002-207763

(51) Int. Cl.⁷ ................................................ G09G 5/00
(52) U.S. Cl. ........................... 702/183; 702/23; 702/30; 702/31; 702/32; 702/187; 702/188
(58) Field of Search ............................. 702/23, 27, 28, 702/30–32, 50, 75, 100, 108, 114, 119–123, 179, 183, 187, 188, FOR 115–FOR 119, FOR 166–168, FOR 121, FOR 127, FOR 128, FOR 134–135, FOR 139, FOR 155–163, FOR 170, FOR 171; 707/1, 102, 104.1, 203, 200; 422/62, 63, 65, 67, 68.1; 382/128, 129, 130, 131, 132, 133

(56) References Cited

U.S. PATENT DOCUMENTS 6,285,498 B1 * 9/2001 Mayer ........................ 359/392
6,366,924 B1 * 4/2002 Parce ........................ 707/104.1
6,528,787 B2 * 3/2003 Katagami et al. ........... 250/310
6,581,012 B1 * 6/2003 Aryev et al. .................. 702/22
6,581,020 B1 * 6/2003 Buote et al. ................. 702/123
6,599,476 B1 * 7/2003 Watson et al. ................. 422/63
2002/0049694 A1 * 4/2002 Parce ............................. 707/1
2002/0049782 A1 * 4/2002 Herzenberg et al. ..... 707/500.1
2002/0059326 A1 * 5/2002 Bernhart et al. ............ 707/203
2002/0095419 A1 * 7/2002 Parce .......................... 707/10
2003/0100995 A1 * 5/2003 Loraine et al. ............... 702/19
2003/0139886 A1 * 7/2003 Bodzin et al. ................ 702/28
2003/0193517 A1 * 10/2003 Cable .......................... 345/716

FOREIGN PATENT DOCUMENTS

JP          09200803          7/1997

* cited by examiner

Primary Examiner—Marc S. Hoff
Assistant Examiner—Carol S W Tsai
(74) Attorney, Agent, or Firm—Webb Ziesenheim Logsdon Orkin & Hanson, P.C.

(57) ABSTRACT

The present invention relates to a method and system for managing data. The invention is intended to provide a data managing method and data managing system capable of classifying created files and managing them without depending on the operator's ability. The method is for use in an analytical instrument having a function of imaging a specimen and a function of analyzing the specimen. The area of the specimen from which the image has been taken is analyzed totally or partially. The analytical instrument includes an analytical data managing unit for recording the resulting data hierarchically in a corresponding manner to the specimen area.

12 Claims, 15 Drawing Sheets

PROJECT
└── SAMPLE
    ├── FIELD OF VIEW 1
    │   │   ┌─────────────────────────────────────────┐
    │   │   │ MAGNIFICATION : 100                     │
    │   │   │ ACCELERATING VOLTAGE : 20 kV            │
    │   │   │ STAGE COORDINATES : (X1,Y1,Z1) mm       │
    │   │   │ SIZE OF THE FIELD OF THE VIEW: (W1 X H1)mm │
    │   │   └─────────────────────────────────────────┘
    │   └── IMAGE 1
    │       ┌─────────────────────────────────────────┐
    │       │ ANALYSIS POSITION: (0,0)-(W1,H1)        │
    │       │ ANALYSIS KIND: SEI                      │
    │       │ KEYWORD: KEY                            │
    │       │ FILE NAME: C:¥PROJECT ¥ SEI1.img        │
    │       └─────────────────────────────────────────┘
    ├── FIELD OF VIEW 2
    │   │   ┌─────────────────────────────────────────┐
    │   │   │ MAGNIFICATION : 200                     │
    │   │   │ ACCELERATION VOLTAGE : 20 kV            │
    │   │   │ STAGE COORDINATES : (X2,Y2,Z2) mm       │
    │   │   │ SIZE OF THE FIELD OF THE VIEW: (W2,W2)mm │
    │   │   └─────────────────────────────────────────┘
    │   └── IMAGE 2
    │       ┌─────────────────────────────────────────┐
    │       │ ANALYSIS POSITION: (0,0)-(W2,H2)        │
    │       │ ANALYSIS KIND: SEI                      │
    │       │ KEYWORD: KEY                            │
    │       │ FILE NAME: C:¥PROJECT ¥ SEI2.img        │
    │       └─────────────────────────────────────────┘
    ├── FIELD OF VIEW 3
    │   └── IMAGE 3
    └── FIELD OF VIEW 4
        └── IMAGE 4

*FIG. 8*

```
PROJECT
    |
    |———— SAMPLE
              |
              |——— FIELD OF
              |    VIEW 1      | MAGNIFICATION : 100                        |
              |                | ACCELERATING VOLTAGE : 20 kV               |
              |                | STAGE COORDINATES : (XI,YI,ZI) mm          |
              |                | SIZE OF THE FIELD OF THE VIEW: (WI,HI)mm   |
              |
              |——— IMAGE 1     | ANALYSIS POSITION: (0,0)-(WI,HI)mm         |
              |                | ANALYSIS KIND: SEI                         |
              |                | KEYWORD: KEY                               |
              |                | FILE NAME: C:\PROJECT \ SEI1.img           |
              |
              |——— RESULT      | ANALYSIS POSITION: (0,0)-(WI,HI)mm         |
                               | ANALYSIS KIND: WORD                        |
                               | KEYWORD: KEY                               |
                               | FILE NAME: C:\XXX \ RESULT.doc             |
```

*FIG.13B*

METHOD AND SYSTEM FOR MANAGING DATA

FIELD OF THE INVENTION

The present invention relates to a data management method and also to a data management system.

DESCRIPTION OF RELATED ART

When data is obtained by measurements using an electron microscope, X-ray analysis apparatus, or the like having analytical capabilities, it has been customary that the operator creates a file name for each item of the data and stores the data in a storage means. Furthermore, the obtained data is classified, depending on the operator's judgment.

As mentioned previously, the operator has been required to determine unique rules and save data or perform operations consciously of the rules to interrelate and classify data. Therefore, the prior art method has the problem that data management depends on the operator's ability and skill level (i.e., planning power and degree of alertness).

SUMMARY OF THE INVENTION

It is an object of the present invention to provide a method and system for classifying and managing obtained data regardless of the operator's ability.

A data management method according to the present invention is implemented using an analytical instrument having a function of imaging a specimen and a function of analyzing the specimen. This method starts with collecting operation-setting information including information about the position of a desired area on the specimen and information about conditions under which the desired area is imaged. The operation-setting information is stored in memory as information records. Then, the desired area on the specimen is analyzed. Data obtained by the analysis is stored in memory as analytical data records. The information records and analytical data records are recorded hierarchically while placing the information records at a higher level of hierarchy.

In one feature of this data management method, the data management records incorporate analytical conditions corresponding to the data obtained by the analysis.

In another feature of the data management method, there is another process step of imaging the desired area on the specimen and storing data about the obtained image in memory as image data records. The information records, and the image data records are recorded hierarchically while placing the information records at a higher level of hierarchy.

In a further feature of the data management method, the analytical data records and the image data records are recorded at the same level of hierarchy.

In still another feature of the data management method, there is another process step of obtaining additional data about the desired area on the specimen and recording the additional data as additional data records. The information records and the additional data records are recorded hierarchically while placing the information records at a higher level of hierarchy.

In a still further feature of the data management method, at least one kind of the analytical data records and the image data records is recorded at the same level of hierarchy as the additional data records.

In an additional feature of the data management method, the analytical instrument is an electron microscope or electron probe microanalyzer having X-ray analysis capabilities.

The present invention also provides a data management system for use in an analytical instrument having a function of imaging a specimen and a function of analyzing the specimen. This data management system comprises: means for collecting operation-setting information including information about the position of a desired area on the specimen and information about conditions under which the desired area is imaged; means for storing the operation-setting information in memory as information records; means for analyzing the desired area on the specimen to thereby obtain data and storing the obtained data as analytical data records in memory; and means for recording the information records and analytical data records hierarchically while placing the information records at a higher level of hierarchy.

In one feature of this data management system, the data records incorporate analytical conditions corresponding to the data obtained by the analysis.

In another feature of the data management system, the system further includes: means for imaging the desired area on the specimen and storing data about the obtained image in memory as image data records; and means for recording the information records and the image data records hierarchically while placing the information records at a higher level of hierarchy.

In a further feature of the data management system, the analytical data records and the image data records are recorded at the same level of hierarchy.

In still another feature of the data management system, the system further includes: means for obtaining additional data about the desired area on the specimen and recording the obtained additional data as additional data records; and means for recording the information records and the additional data records hierarchically while placing the information records at a higher level of hierarchy.

In a still further feature of the data management system, at least one kind of the analytical data records and the image data records is recorded at the same level of hierarchy as the additional data records.

In an additional feature of the data management system, the analytical instrument is an electron microscope or electron probe microanalyzer having X-ray analysis capabilities.

Because of the structure described thus far, files can be automatically created from data obtained by measurements, automatically classified, and stored in memory. In consequence, data can be managed regardless of the operator's skill level.

Other objects and features of the invention will appear in the course of the description thereof, which follows.

BRIEF DESCRIPTION OF THE DRAWINGS

FIG. 8 is a diagram showing the hierarchical structure of data in a condition prior to analysis;

FIGS. 13A and 13B are diagrams showing the hierarchical structure of data according to the present invention, the structure being created as a result of execution of the sequence of operations illustrated in FIG. 12.

DESCRIPTION OF THE PREFERRED EMBODIMENTS

A first embodiment of the present invention is hereinafter described in detail with reference to the accompanying drawings.

Figure 1:
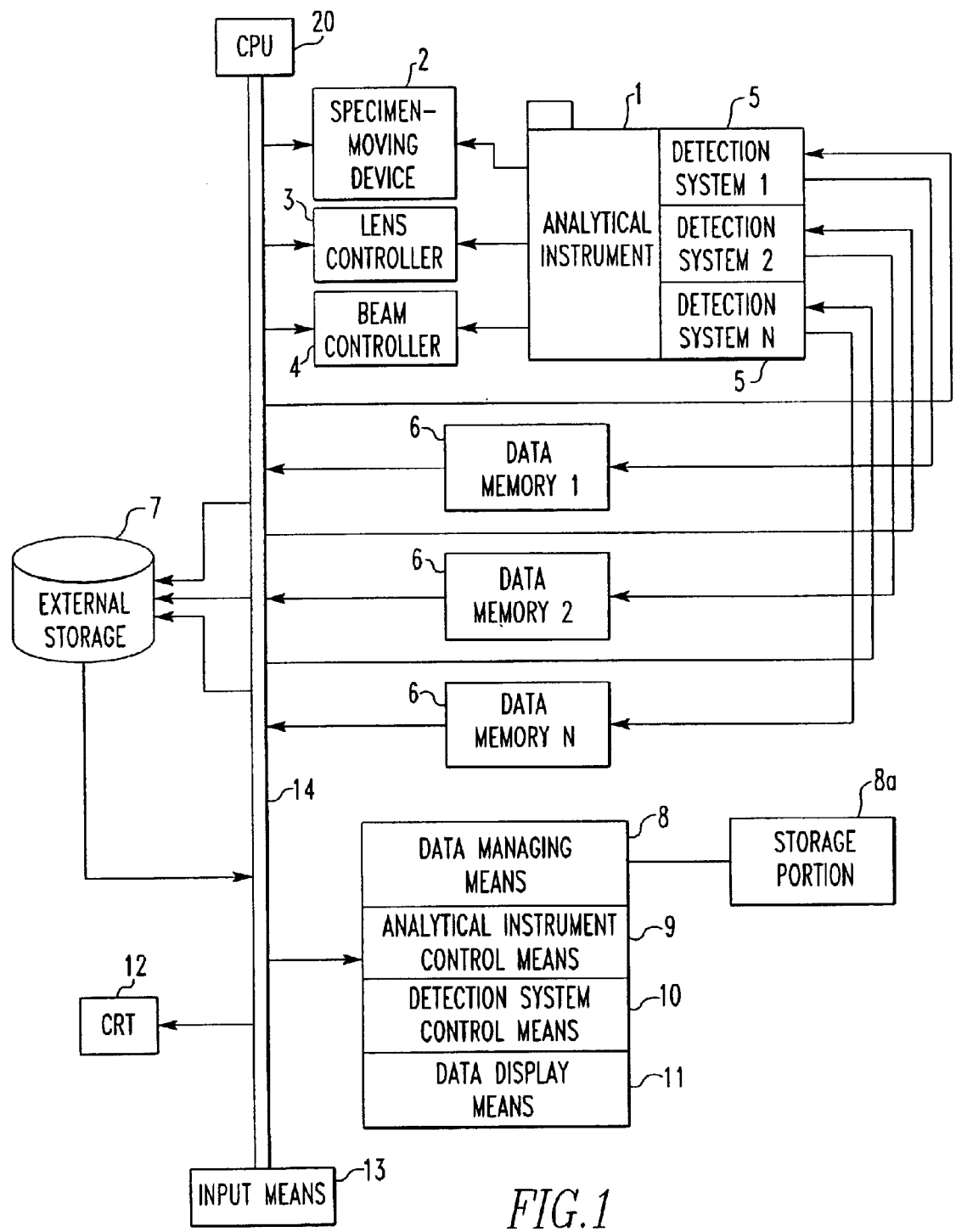
FIG. 1 is a block diagram of a system for implementing the present invention.

FIG. 1 is a block diagram of a data management system for implementing the present invention. The system includes an analytical instrument 1, such as a scanning electron microscope (SEM), equipped with X-ray analysis apparatus. A specimen analyzed by the analytical instrument 1 is moved by a specimen-moving device 2 consisting of a sample stage. A lens, such as an electron lens, within the analytical instrument 1 is controlled by a lens controller 3. A beam, such as an electron beam, within the analytical instrument 1 is controlled by a beam controller 4. These specimen-moving device 2, lens controller 3, and beam controller 4 are used when the specimen is analyzed by the analytical instrument 1.

N detection systems 5 (detection systems 1 to N) for detecting various signals emanating from the specimen are mounted to the analytical instrument 1. SEM image signals, X-ray analysis signals, elemental analysis signals, and so on are detected by these detection systems 5. Signals detected by the detection systems 5 are stored in N data memories 6 (data memories 1 to N) which are equal in number with the detection systems 5.

Various kinds of data are stored in an external storage 7, such as a hard disk drive. An analytical data managing means 8 has a storage portion 8a. Also shown are an analytical instrument control means 9, a detection system control means 10, and a data display means 11. These means can be implemented both in hardware and in software.

A CRT 12 acts as a display means for displaying various kinds of information. An input means 13, such as a keyboard and a mouse, are used to enter various kinds of information and signals indicating coordinate positions. A bus 14 is used to interconnect the various components. A control means 20, such as a CPU, controls the whole system. The operation of the data management system constructed in this way is described below.

Where a specimen is analyzed by a scanning electron microscope fitted with X-ray analysis apparatus, the specimen is inserted into the specimen chamber within the microscope. The specimen is moved or the magnification is adjusted while observing a secondary electron image, for example, of the specimen. An image is obtained in such a way that an area or point to be analyzed is brought into the field of view. Then, the operator specifies a certain area or point within the image. Subsequently, a desired analysis, such as elemental analysis of the certain point or mapping analysis of a certain element, is carried out. In this case, data is obtained from the secondary electron image or data is derived by point analysis or mapping analysis.

Figure 2:
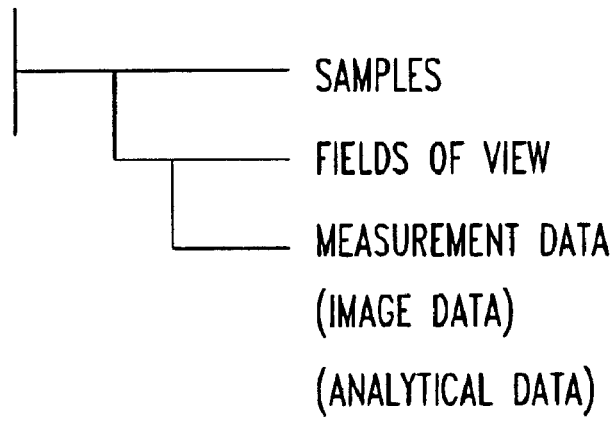
FIG. 2 is a diagram illustrating one example of hierarchical structure of data management according to the present invention.

FIG. 2 is a diagram illustrating an example of hierarchical structure for data management in analytical data management means for recording and managing data obtained by such measurements or analyses. As shown, the hierarchical structure consists of "projects" at the first level of hierarchy, "samples" at the second level of hierarchy, "fields of view (FOVs)" at the third level of hierarchy, and "measurement data" at the fourth level of hierarchy. This hierarchical structure is placed and stored in the storage portion 8a of the analytical data managing means 8. In this example, each project contains one or more samples. One or more fields of view are specified for each sample. Each field of view contains one or more items of data obtained by performing a measurement within the field of view.

Figure 3A:
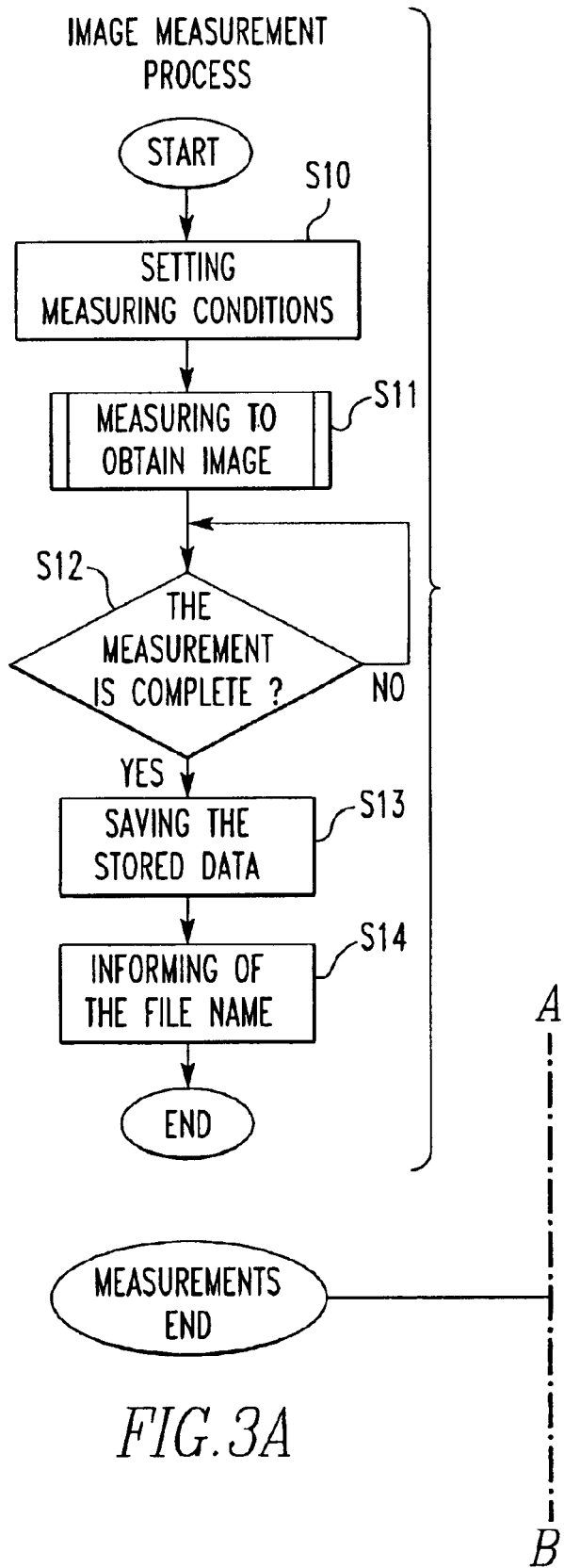
FIGS. 3A and 3B together are a flowchart illustrating a method of creating field of view (FOV) records and data records according to the present invention.
Figure 3B:
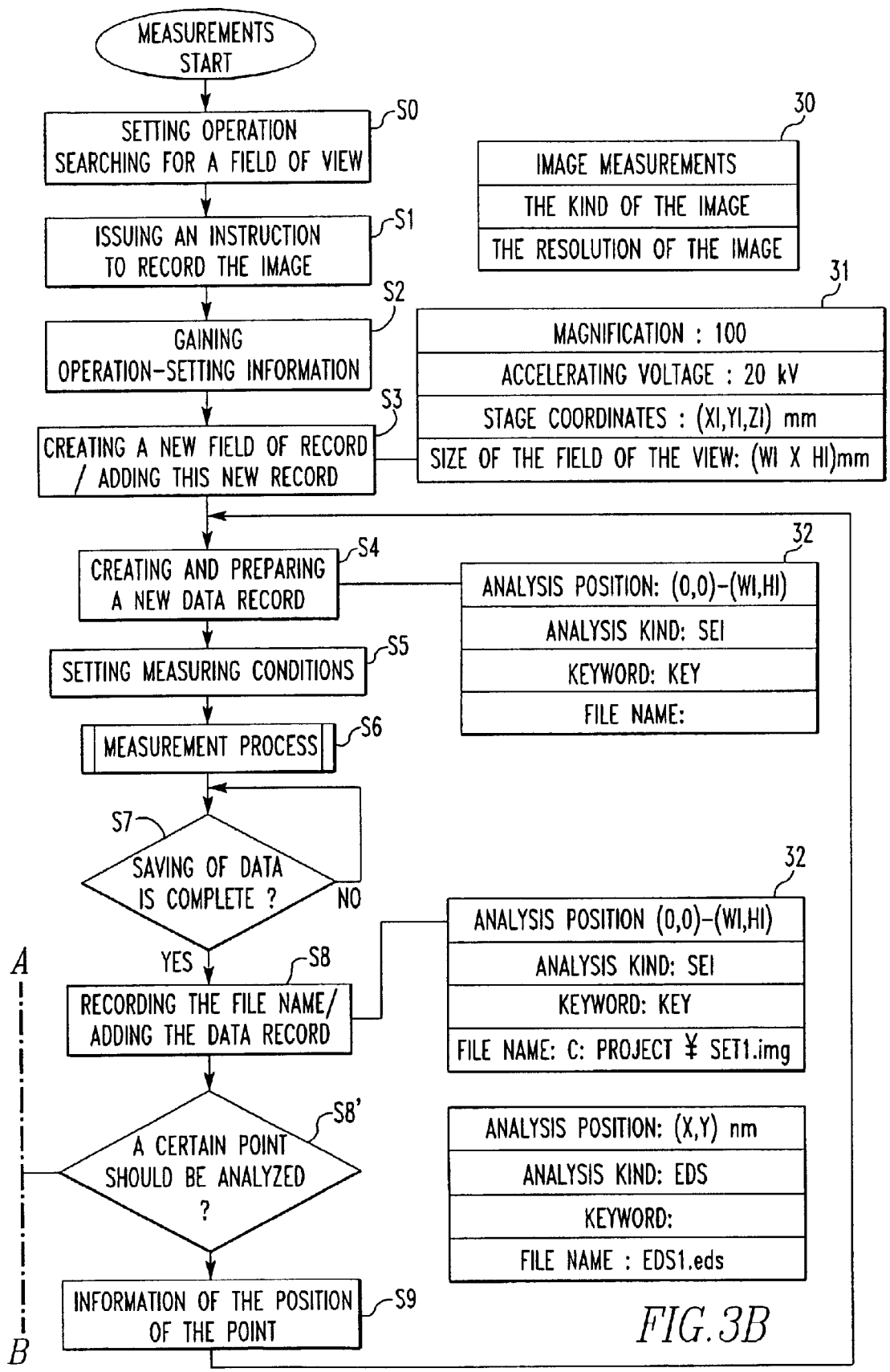

FIGS. 3A and 3B together are a flowchart illustrating the manner in which field of view records (FOV records) and data records are created according to the present invention. The method of managing data in the present embodiment is hereinafter described in detail. First, a setting operation regarding an image of a specimen is performed to search for a desired field of view (step S0). For example, as indicated by reference numeral 30, the kind of the image (normally, either a BEI (backscattered electron image) or SEI (secondary electron image) is used) is set. Also, the resolution or the number of pixels of the image is set.

If an SEI is selected, the operator adjusts various conditions including the accelerating voltage to obtain a good secondary electron image. A search for field of view is started regarding sample 1. In practice, the operation is started, for example, at a low magnification that provides a wider field of view. The sample is moved. The searched area is gradually narrowed down until a characteristic portion of a desired area on the sample is placed within one field of view and a good secondary electron image is obtained. When this state is obtained, the operator issues an instruction to record the image (S1).

Receiving the instruction for recording of this image, the analytical data managing means 8 gains information (operation-setting information) regarding the present conditions under which the apparatus is operated from the analytical instrument control means 9 (step S2). The gained information includes information about the position of a desired area on the specimen and information about the conditions under which the desired area is imaged. For example, the information includes the beam accelerating voltage, the coordinates (X1, Y1, Z1) (in mm) of the sample stage, the magnification, and the size of the field of view (W1, H1) (in mm).

Then, the analytical data managing means 8 creates a new field of view record 31 based on the information obtained in step S2, the field of view record 31 being an information record. The data managing means 8 adds this new record to the sample 1 (at a higher level of hierarchy) of the data hierarchical structure stored in the storage portion 8a of the analytical data managing means 8 (step S3). The contents of the new field of view record 31 are the aforementioned operation-setting information and consist of magnification, accelerating voltage, stage coordinates, size of the field of view, and so on as shown in FIGS. 3A–3B.

Then, the analytical data managing means 8 creates and prepares a data record 32 to be newly recorded (step S4). The new data record 32 consists of analysis position, analysis kind (SEI (secondary electron image) in this example), keyword for searching, and data file name. Since the analysis position is given by relative coordinates within the field of view and located in the same area as the field of view, the analysis position is given by ((0, 0)–(W1, H1)). The file name is not yet written because data about an image is not yet obtained by measurement.

Since an empty data record of image data has been completed in this way, measuring conditions are set for a measurement process as a process step prior to measurement for obtaining image data (step S5). In particular, the measuring conditions were set and obtained in steps S0 and S2.

When the measurement process is entered, conditions are entered into the detection systems 5 and then the measurement is started (step S6). This will be described in further detail later. Since this measurement is performed to obtain a secondary electron image, it is obvious that the detection system for detecting secondary electrons is used. During the measurement process, a measurement is performed. As a result, image data is obtained. The data is once stored in the data memories 6. Thereafter, the image data is read from the data memories 6 and recorded in the external storage 7 as a data file having a file name. The analytical data managing means 8 is informed of this file name used during the recording.

If the analytical data managing means 8 confirms that saving of the data obtained by the measurement is complete in step S7, the file name given to the managing means 8 during the measurement process is recorded in the already prepared data record 32. This data record 32 is added under directory "field of view 1" that is a collection of information records in the data hierarchical structure stored in the storage portion 8a of the analytical data managing means 8 (step S8). In the indicated data record 32, "C:\project\SEI1.img" is registered as the file name, as an example. Consequently, the data record 32 and the data file derived by an actual measurement and stored in the external storage 7 are interrelated via the file name. Data about an image obtained by a measurement is stored as the image data record 32. The information record and image data record are recorded hierarchically such that the information record is placed at a higher level of hierarchy.

The measurement process S6 is next described in detail. First, measuring conditions are set (S10). A measurement is performed by the detection systems 5 to obtain an image (S11). A decision is made to check whether the measurement is complete (S12). If the measurement is complete, data obtained by the measurement is temporarily stored in the data memories 6. Then, the temporarily stored data is saved in the external storage 7 as a file having a file name (S13). Thereafter, the measurement process S6 informs the analytical data managing means 8 of the file name (S14). If necessary, the analytical data managing means 8 can read out the measurement data stored in the external storage 7 and cause the data display means 11 to display the data on the CRT 12.

Immediately after measurement and recording of a secondary electron image from the field of view 1 are ended in this way, a decision is made to judge whether a certain point within the field of view 1 should be analyzed (step S8'). If it is not analyzed, the measurement process is ended. If an analysis is then performed, control goes to step S9, where the operator informs the data managing means 8 and analytical instrument control means 9 of the position (coordinates) of the certain point and the kind of the analysis, using the input means 13. After confirming that the field of view remains the same, the analytical data managing means 8 returns to step S4, where the managing means creates a new data record for managing the data obtained by the specified analysis.

Subsequently, control goes back to a measurement process in the same way as the foregoing process. Step S10 for setting measuring conditions is performed. A desired point within the field of view 1 is analyzed by a desired kind of method. As a result of the measurement or analysis, analysis data temporarily stored in the data memory is stored as a data file having a file name of EDS1 in the external storage 7. The analytical data managing means 8 is informed of this file name. The managing means 8 records this file name in a new data record. The new data record in which the file name has been recorded is added under the directory "field of view 1" that is a collection of information records in the hierarchical structure stored in the storage portion 8a of the managing means 8, as parenthesized in FIG. 3B. In consequence, data obtained by analysis is stored as an analysis data record. Then, the information record and the analysis data record are recorded hierarchically while placing the information record at a higher level of hierarchy.

Figure 4:
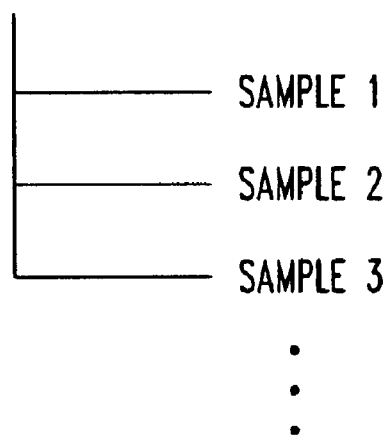
FIG. 4 is a diagram illustrating the hierarchical structure of data prior to measurement.
Figure 5:
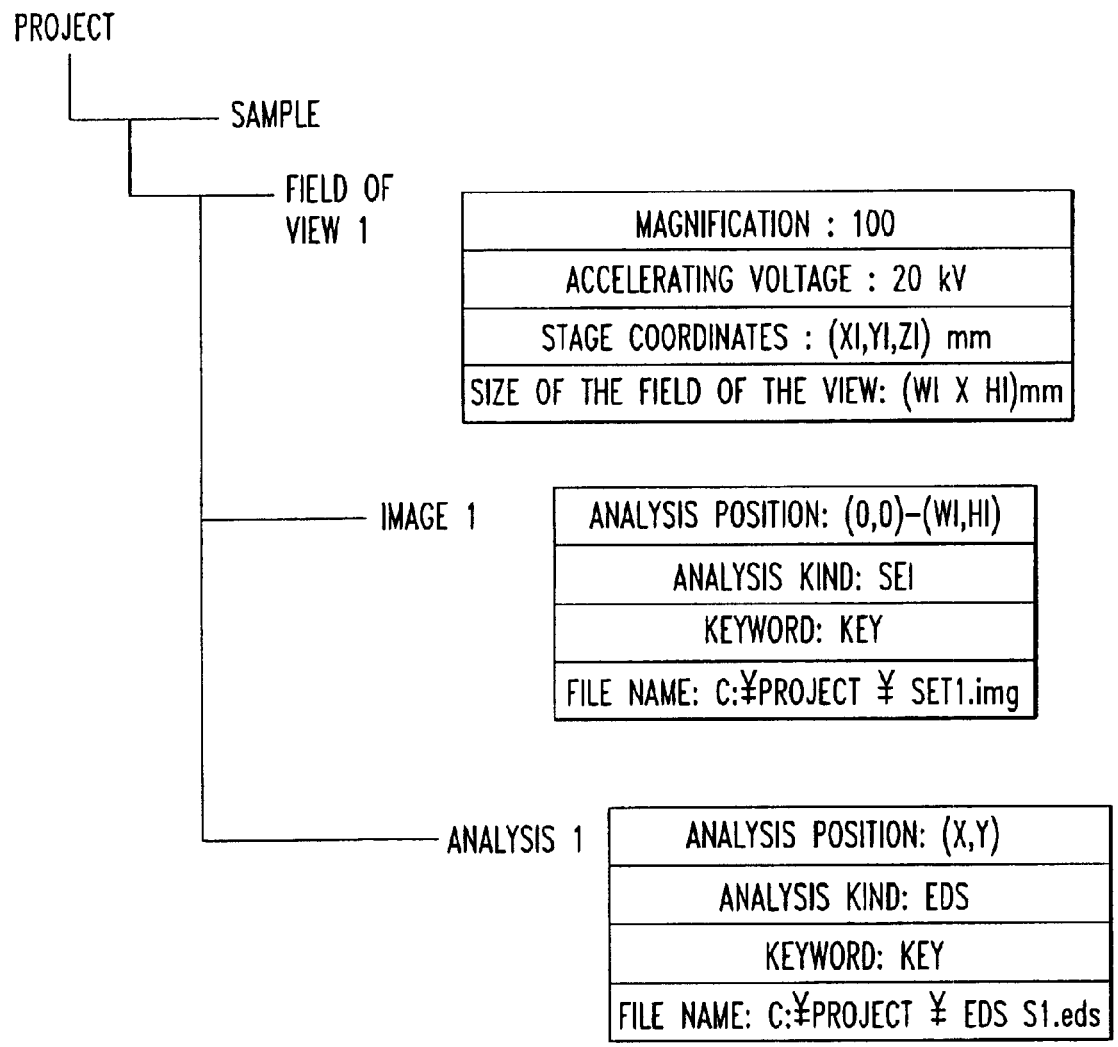
FIG. 5 is a diagram illustrating the hierarchical structure of data after measurement.

FIG. 4 illustrates the data management structure prior to the start of a measurement. FIG. 5 illustrates the data structure after the end of a series of measurements. Before the measurements, a record "project" exists at the first level of hierarchy. Only a record "sample" has been recorded at the second level of hierarchy. Any record of a field of view does not exist at the third level of hierarchy. Also, any record of measurement data does not exist at the fourth level of hierarchy.

In contrast, in the case of FIG. 5, an information record of "field of view 1" is registered at the third level of hierarchy under "sample 1". Image data record "SEI1" of image data and analysis data record "EDS1" of analysis data are registered at the same fourth level of hierarchy under "field of view 1".

In this way, in the present invention, if the operator determines a field of view and performs a series of operations for obtaining an image from the field of view or performing an analysis within the field of view, the analytical data managing means 8 automatically creates records of a hierarchical structure where data obtained by a measurement within the field of view or data obtained as a result of an analysis are successively related with the field of view and managed. Hence, the data can be managed highly efficiently without relying on the operator's skill level.

Figure 6A:
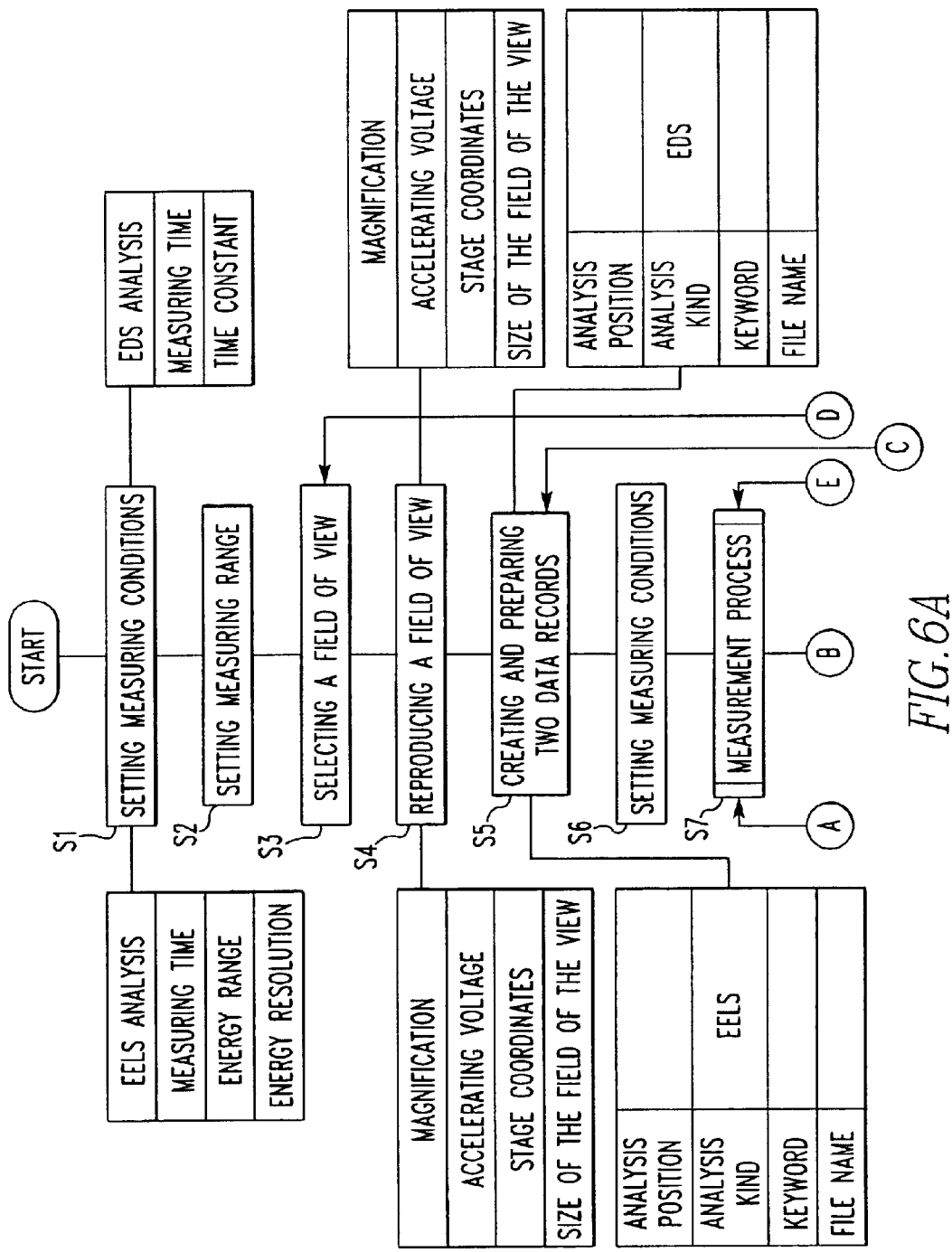
FIGS. 6A, 6B, and 6C together are a flowchart illustrating a method of performing analyses using electron energy loss spectroscopy (EELS) and energy dispersive spectroscopy (EDS) simultaneously according to the present invention.
Figure 6B:
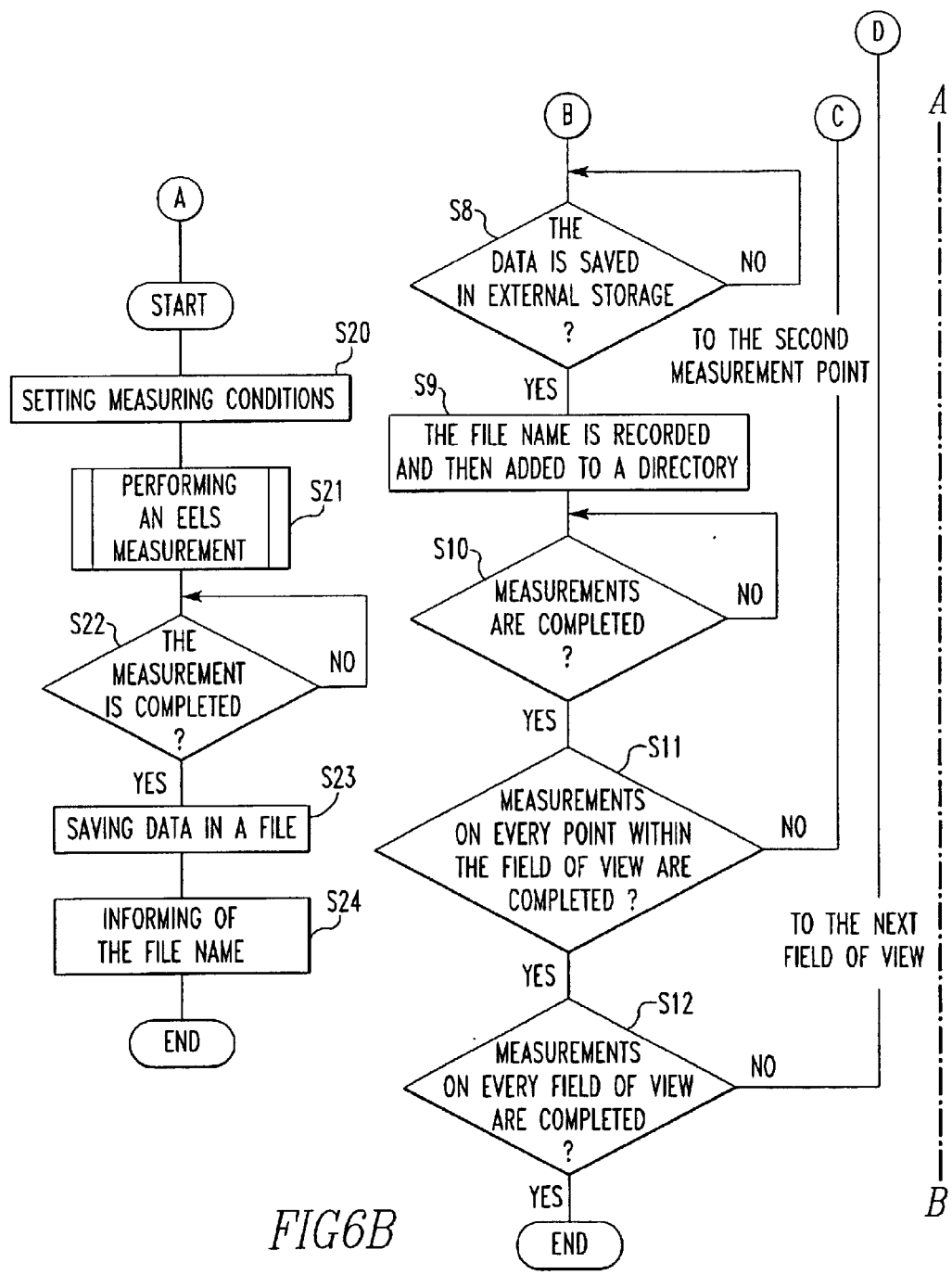
Figure 6C:
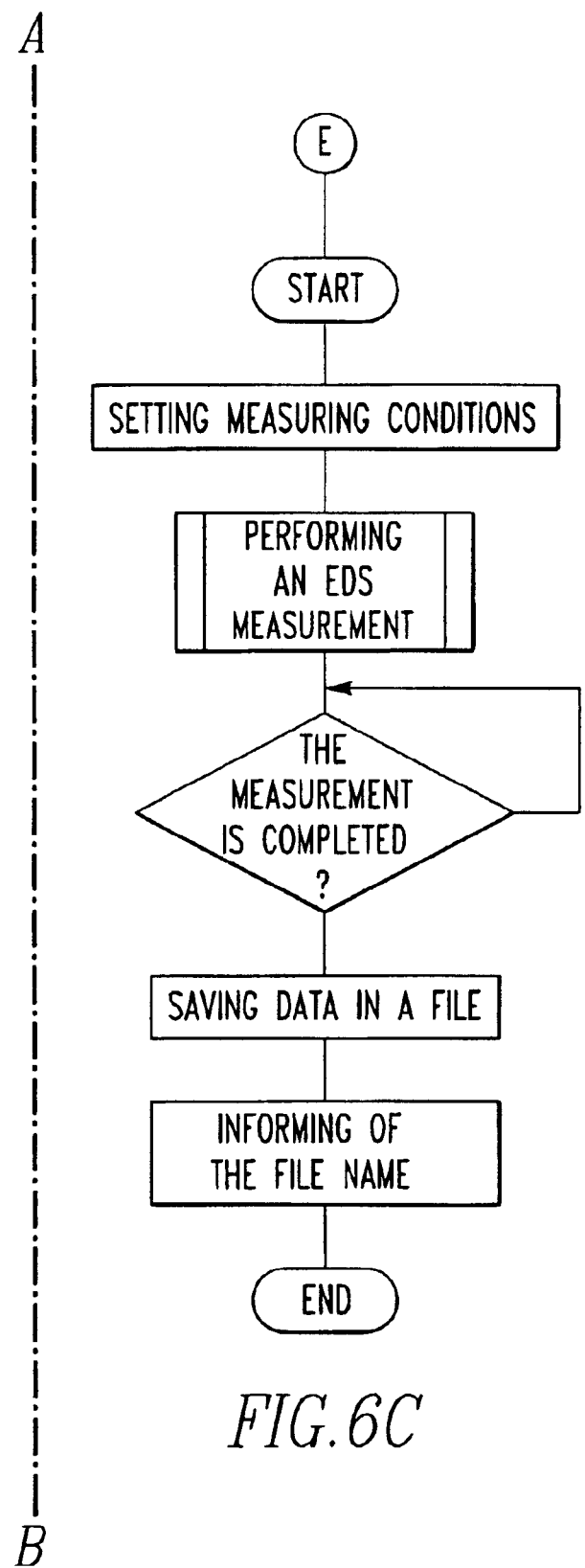

A second embodiment of the present invention is next described by referring to FIGS. 6A and 6B, which are a flowchart illustrating a method of performing analyses using electron energy loss spectroscopy (EELS) and energy dispersive spectroscopy (EDS) simultaneously. It is now assumed that measurements have been made to obtain images from plural fields of view (fields of view 1 to 4) and that data about the images have been recorded. In the flowchart of FIGS. 3A–3B, various processing steps for executing measurements for obtaining data about images and their recordings have been carried out by steps S0 to S9 regarding the four fields of view. This corresponds to a case where the result of the decision made in step S9 is that EELS analysis and EDS analysis are simultaneously carried out. FIGS. 6A–6C show the process by which data is created if an analysis point on the image obtained by a measurement is specified (i.e., where an analysis is performed) and EELS and EDS analyses are performed. A transmission electron microscope is assumed as the apparatus in practice. The EELS detection system measures the energy losses of electrons after the electron beam is transmitted through the specimen. The EDS detection system measures X-rays from above the specimen, the X-rays being produced by the electron beam hitting the specimen. Therefore, simultaneous measurements are permitted.

When the operator issues an instruction to perform EELS and EDS measurements simultaneously, the analytical instrument control means 9 sets measuring conditions for various measurements performed by the analytical instrument 1 (step S1). Normally, standard measuring conditions are previously prepared and can be used. In some cases, the operator can arbitrarily modify desired settings of the previously prepared measuring conditions. One example of measuring conditions using EELS consists of parameters including measuring time, energy range, and energy resolution. An example of measuring conditions using EDS includes measuring time and time constant.

Figure 7:
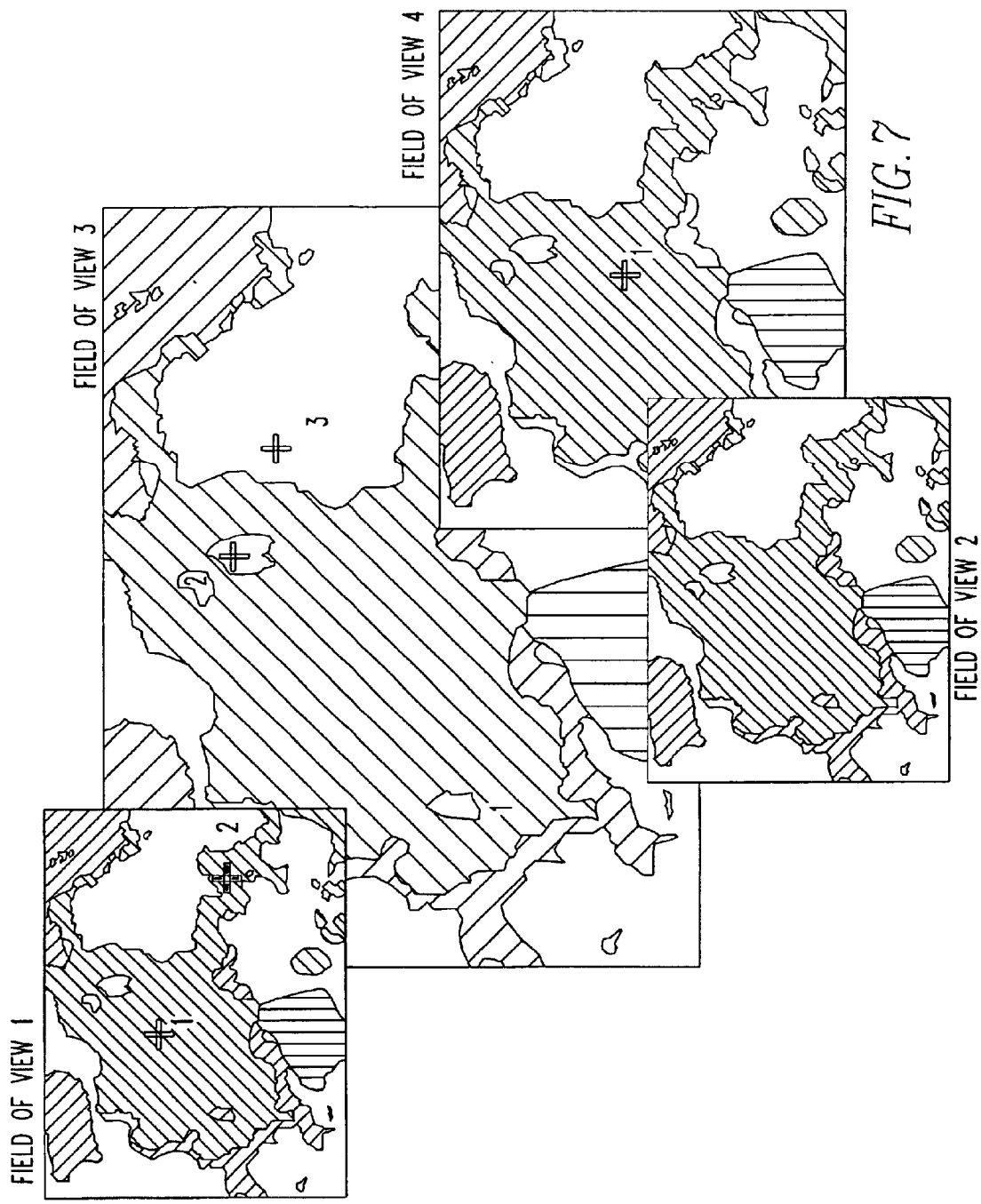
FIG. 7 shows a screen display illustrating the manner in which fields of view and analytical points are set, showing one example of a main window displayed on the viewing screen of a display unit according to the present invention.

Then, in step S2, the operator sets the measuring range. Specifically, as illustrated in FIG. 7, images from the four fields of view, 1 to 4, that have been gained and recorded are read out and displayed on the viewing screen of the CRT 12 concurrently. A point on each image that needs analysis can be specified using the input means, such as a mouse. In the example of FIG. 7, analytical points in the fields of views 1, 3, and 4 are specified. Any analytical point in the field of view 2 is not specified. Accordingly, as a result of this setting operation, information about the fields of view 1, 3, and 4 to be measured and information about the positions (coordinates) of the analytical points in these fields of view are obtained.

Then, the analytical data managing means 8 selects a field of view on which a first measurement is made, based on the information (step S3). It is assumed that a lower numbered field of view is selected earlier. Accordingly, in the present embodiment, the field of view 1 is selected first. Then, the analytical data managing means 8 reproduces a state prior to measurement concerning the selected field of view 1 (e.g., a measurement for obtaining an image). As mentioned previously, information including accelerating voltage, stage coordinates, and magnification is recorded in an information record of the field of view 1. Therefore, this information is read from the record of the field of view 1 and sent to the analytical instrument control means 9, which in turn sets conditions for the analytical instrument based on the information. For example, the stage is moved, and the accelerating voltage is modified. In this way, the state prior to measurement concerning the field of view 1 is reproduced (step S4).

In this example, two kinds of analyses are simultaneously performed using EELS and EDS and so the analytical data managing means 8 creates and prepares two data records (S5). The position (coordinates), the kind of analysis, a keyword, etc. are recorded in each data record. The coordinates of each analysis point are represented in terms of a system of coordinates whose origin lies within the field of view. Then, the analytical data managing means 8 sets measuring conditions for each measurement process (S6). That is, the measuring conditions set in step S1 and the analysis point specified in step S2 are incorporated into the measurement process. Then, the measurement process is started (step S7). This step will be described in detail later. In each measurement process, as soon as a measurement ends, a file name is automatically given to the obtained data. The data is then saved as a data file in the external storage 7. The analytical data managing means 8 is informed of the saved file name. The analytical data managing means 8 checks whether data is saved in the external storage 7 (S8). If data is saved, the saved file name is recorded in the prepared data record. The data record is added to a directory that is under the records of the field of view 1 in the hierarchical structure stored in the storage portion 8a of the analytical data managing means 8 (S9).

Then, the analytical data managing means 8 checks whether both EELS and EDS measurements are completed (S10). If both are completed, measurements are continued on every measurement point within the field of view (S11). For example, if there are two measurement points within the field of view 1, the measurement on the second measurement point is not yet finished. Therefore, control goes back to step S5, where a measurement on the second measurement point is performed.

If the result of the decision made in step S11 is that measurements on every measurement point within this field of view are completed, then the analytical data managing means 8 checks whether measurements on every field of view have been completed (S12). In this case, there are three fields of view (i.e., 1, 3, and 4) on which measurements are performed and so control returns to step S3, where the next field of view (field of view 3 in this example) is selected and then the measuring sequence is repeated.

A measurement process using EELS is described. First, measuring conditions are set (S20). An EELS measurement is performed (S21). The instrument waits until the measurement is completed (S22). Then, data obtained by the measurement is saved in a file (S23). The analytical data managing means 8 is informed of the file name of the saved data (S24). As a result, an EELS spectrum is stored in the external storage 7. The file name of the stored data is registered in a data record. While EELS has been described thus far, the principle is the same in the case of EDS.

In the embodiment described above, EELS and EDS measurements are performed at the same time. Exactly the same data will be obtained if these two kinds of measurements are carried out in turn.

The manner in which data about the field of view 1 is created is described below. FIG. 7 illustrates fields of view and the manner in which analysis points are established. FIG. 7 is one example of a main window displayed on the viewing screen of a display unit according to one embodiment of the present invention.

FIG. 8 shows the hierarchical structure stored in the storage portion 8a of the analytical data managing means 8 prior to the start of an analysis. A record "project" exists at the first level of hierarchy. A record "sample" exists at the second level of hierarchy. Records of the fields of views 1 to 4 exist at the third level of hierarchy. With respect to the field of view 1, a record "image 1" is formed at the underlying fourth level of hierarchy. Analysis position, kind of analysis, keyword, and file name have been written.

Figure 9:
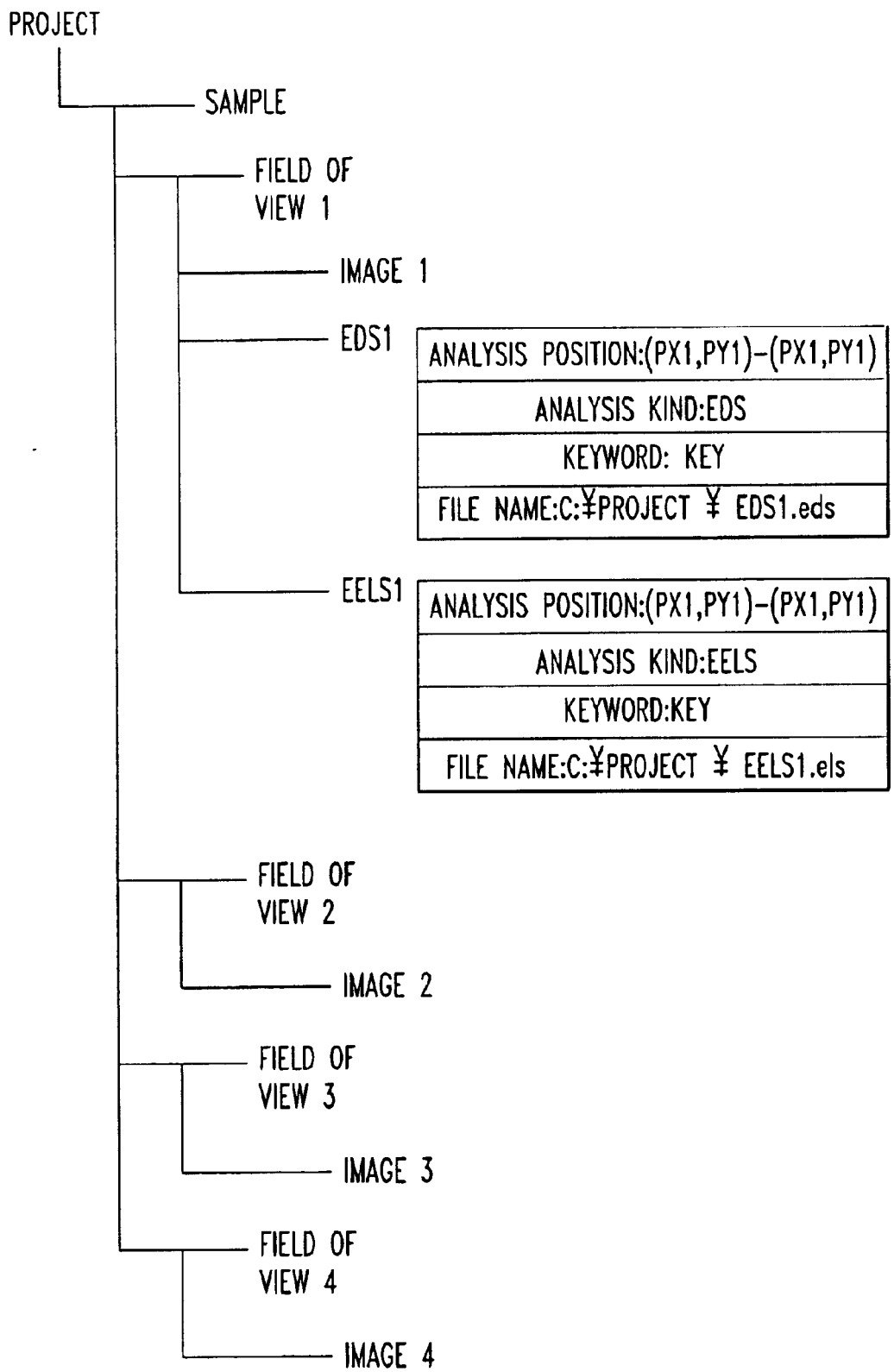
FIG. 9 is a diagram of the hierarchical structure of data when a measurement about one analytical point has ended.

FIG. 9 shows the above-described hierarchical structure when a measurement on one analysis point has ended. With respect to the field of view 1, an EDS data item, EDS1, and an EELS data item, EELS1, derived from the first measurement point are formed. The starting point and the end point are identical and lie at (Px1, Py1)–(Px1, Py2). This indicates that the analysis position is a point. Items of data obtained by these analyses are managed under file names "c:\project\EDS1.eds" and "c:\project\EELS1.els", respectively. Their detail data are stored as data files having the aforementioned file names in the external storage 7. Therefore, the data can be read out as the need arises.

Figure 10:
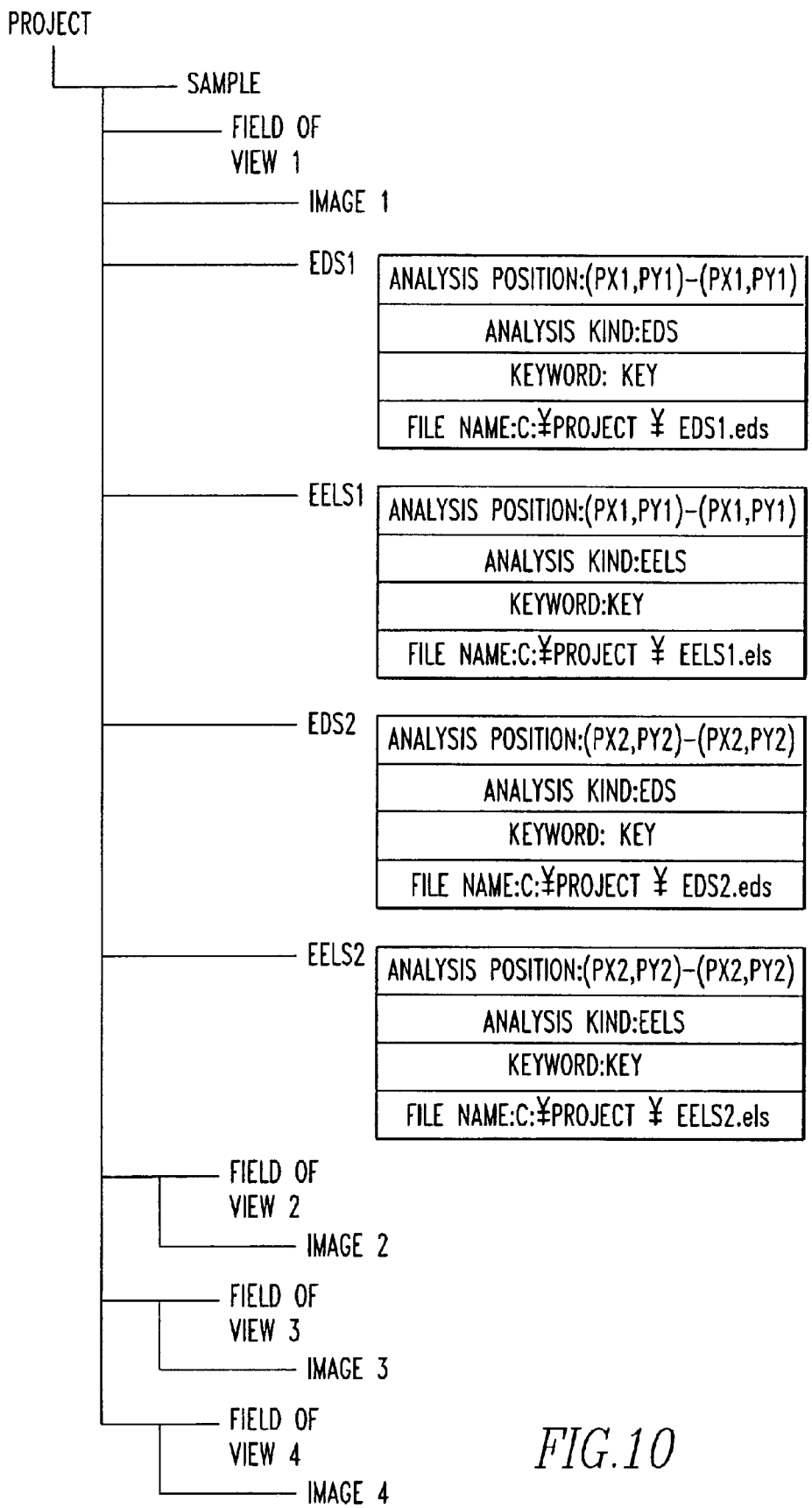
FIG. 10 is a diagram of the hierarchical structure of data when a measurement about field of view 1 has ended.

FIG. 10 shows the state in which a measurement on the field of view 1 has ended. As mentioned previously, there are two measurement points in the field of view 1. Accordingly, EELS data items and EDS data items (EELS1, EELS2, EDS1, and EDS2) about the two points have been written. It is shown that measurements on the two analysis points have ended. The present invention is characterized in that data obtained by measurement are automatically classified by a category of field of view.

Figure 11:
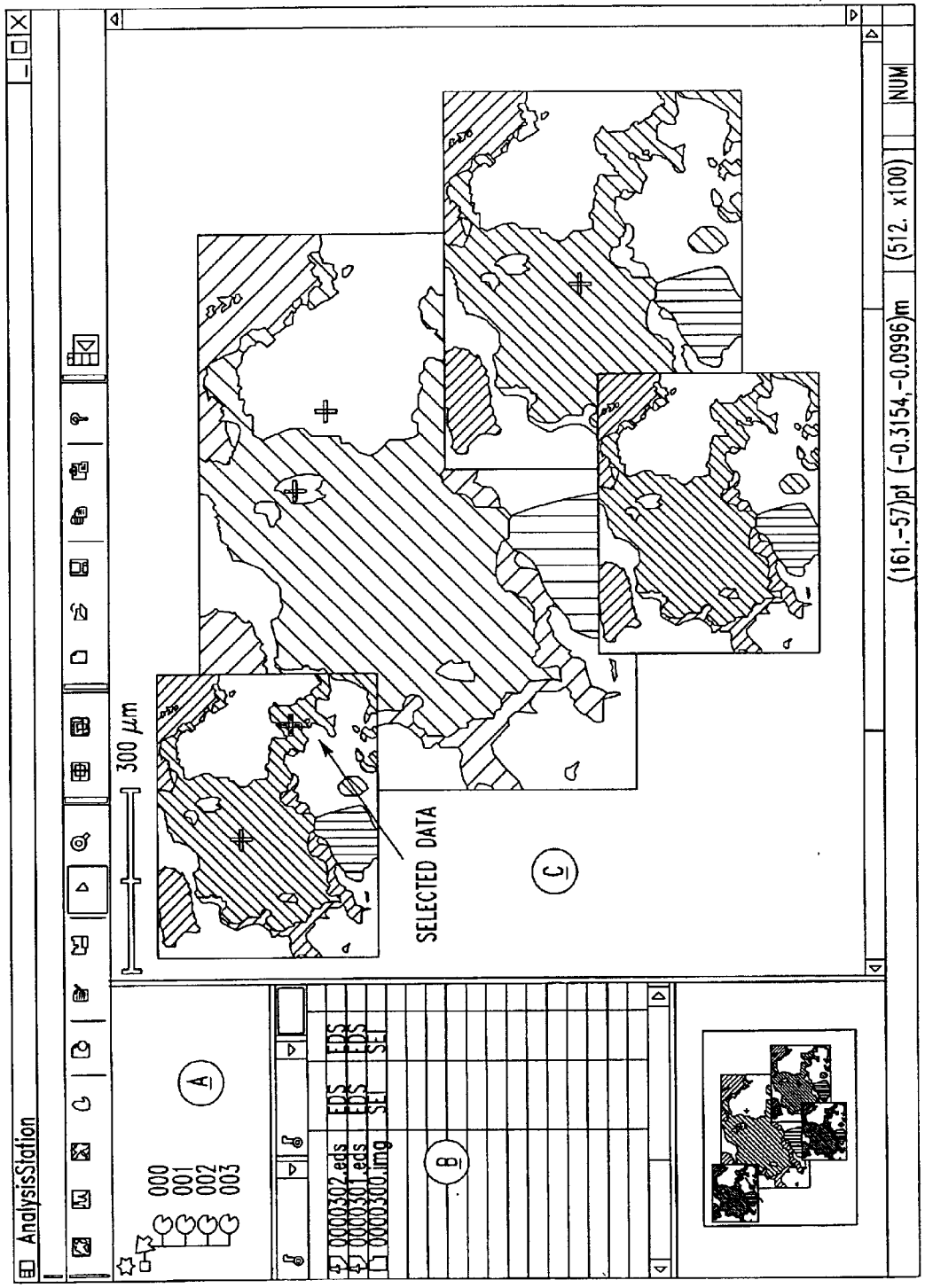
FIG. 11 shows a screen display of a management window for managing obtained data, showing one example of a main window displayed on a display unit according to the present invention.

FIG. 11 shows one example of a management window to manage data derived. FIG. 11 is one example of main window displayed on the display unit according to one embodiment of the present invention. This management window is displayed under control of the analytical data managing means 8. The management window is divided into three viewing areas A–C. In the viewing area A, up to three levels "project", "sample", and "field of view" are displayed in a tree-like form. In the area B, a list of data obtained by measurements is displayed. The area C is a data display area where an image or graph created based on the data derived by measurements is displayed.

In the area A, a list of projects is first displayed. If project 1 is selected from the list, project 1 and a list of samples contained in the project are displayed. If sample 1 is selected from the list, all the fields of views 1 to 4 set for sample 1 are displayed over three levels of hierarchy (i.e., project 1-sample 1-field of view) and in a tree-like form as shown in FIG. 11.

At this time, reference images gained for the fields of view 1 to 4 are read out and displayed in arrayed form in the viewing area C as shown in FIG. 11.

If the field of view 1 is selected from the four fields of view displayed in the area A, a list of the file names of three data items which have been obtained by measurement about the field of view 1 and are stored is displayed in the area B as shown in FIG. 11.

If a file "0000302.eds", for example, is selected from the list of data items displayed in the area B, and if an instruction to display the file is given, the selected file is read from the external storage 7. Based on the read EDS data, an EDS spectrum obtained from a certain analysis point by an EDS measurement is displayed in the viewing area C. Where the selected file consists of mapping data obtained by a mapping measurement, a mapping image is displayed in the viewing area C. In this way, an appropriate display format is selected according to the selected file format.

Figure 12:
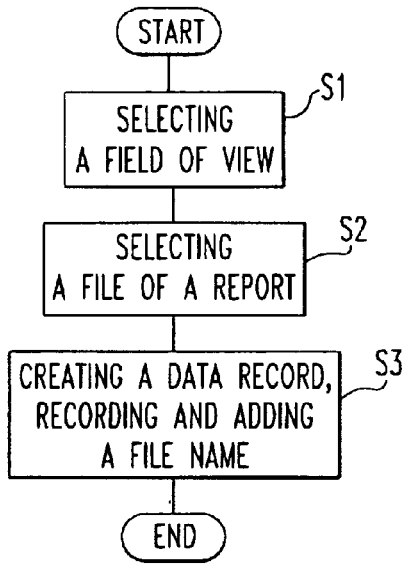
FIG. 12 is a flowchart illustrating a sequence of operations for registering already existing files in a field of view.

FIG. 12 is a flowchart illustrating a sequence of operations for registering an already existing file in a field of view. It is assumed that if a report about the same field of view is created by a separate unit, a file of the report is written to a flexible disk or the like. Then, the disk is transported. The report is gained and registered as a report about the same field of view. Referring to the flowchart of FIG. 12, a field of view is selected (S1). A file of a report to be added is selected (S2). Then, the analytical data managing means 8 creates a data record as a report data record. Its file name is recorded and added to the field of view (S3).

Figure 13A:
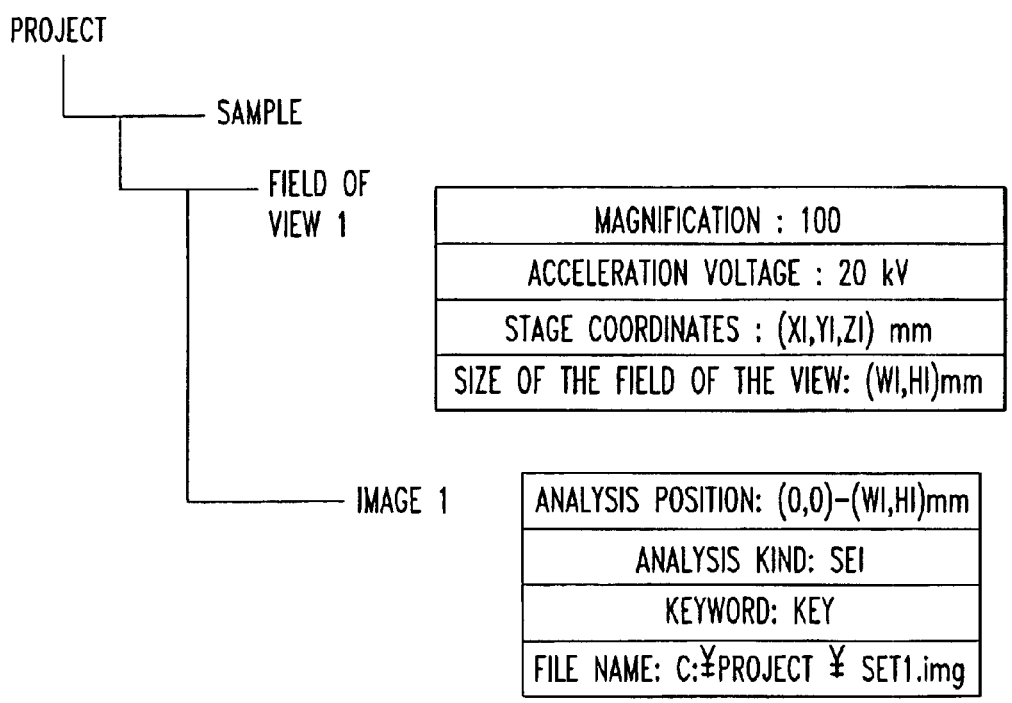

FIGS. 13A-3B show the data structure created by performing the sequence of operations illustrated in FIG. 12 according to the present invention. FIG. 13A indicates the state prior to registration. FIG. 13B indicates the state after the registration has been made. It can be seen that in the state shown in FIG. 13B, data records created in step S3 have been registered at a level under the field of view 1 that is a collection of information records. Registered file names of data records are given by c:\XXX\result.doc. Thus, report data (additional data) about a desired area on a specimen is gained and recorded as report data records (additional data records). The information records and report data records are recorded hierarchically while placing the information records at a higher level of hierarchy.

In the example shown in FIG. 13B, report data records are recorded at the same level of hierarchy as image data records. Report data records may be recorded at the same level of hierarchy as analysis data records.

Their file names are displayed in FIG. 1B. If one of the file names is selected, wordprocessor software is activated according to the kind of the file, and the text of the report is displayed in FIG. 11C.

In the embodiment above, there is one image within one field of view. The number of images belonging to one field of view is not limited to one. For instance, other images taken from a small area of interest within the field of view 1 may be registered as images 1–2, 1–3, etc. within the field of view 1.

It is to be understood that the present invention is not limited to the embodiments above. Rather, various changes and modifications are possible. For example, the data managing system according to the present invention can be operated remotely from the analytical instrument by replacing the bus interconnecting the components shown in FIG. 1 by a network. Furthermore, the above-described method and system for data management can also be applied to an electron probe microanalyzer equipped with a wavelength dispersive spectrometer.

As described thus far, the present invention can offer a data management system capable of classifying and managing obtained data without depending on the operator's ability.

Having thus described our invention with the detail and particularity required by the Patent Laws, what is desired protected by Letters Patent is set forth in the following claims.

What is claimed is:

1. A data management method for use in an analytical instrument having a function of imaging a specimen and a function of analyzing the specimen by detecting X-rays from the specimen, said analytical instrument being one of an electron microscope and electron probe microanalyzer having X-ray analysis capabilities, said method comprising the steps of:

collecting operation-setting information including information about position of a desired area on the specimen and information about conditions under which the desired area is imaged;

storing said operation-setting information in memory as information records;

then analyzing said desired area on the specimen by detecting X-rays from the desired area to thereby obtain data; and storing said obtained data as X-ray analysis data records, wherein said information records and said X-ray analysis data records are recorded hierarchically while placing the information records at a higher level of hierarchy.

2. The data management method of claim 1, wherein said X-ray analysis data records incorporate analytical conditions corresponding to the data obtained by the analysis.

3. The data management method of claim 1 or 2, further including the step of imaging said desired area on the specimen to thereby obtain an image and storing data about the obtained image as image data records, and wherein said information records and said image data records are recorded hierarchically while placing the information records at a higher level of hierarchy.

4. The data management method of claim 3, wherein said X-ray analysis data records and said image data records are recorded at the same level of hierarchy.

5. The data management method of claim 1 or 2, further including the step of obtaining additional data about the desired area on the specimen and recording the obtained additional data as additional data records, and wherein said information records and said additional data records are recorded hierarchically while placing the information records at a higher level of hierarchy.

6. The data management method of claim 5, wherein at least one kind of said X-ray analysis data records and said image data records is recorded at the same level of hierarchy as said additional data records.

7. A data management system for use in an analytical instrument having a function of imaging a specimen and a function of analyzing the specimen by detecting X-rays from the specimen, said analytical instrument being one of an electron microscope and electron probe microanalyzer having X-ray analysis capabilities, said data management system comprising:

means for collecting operation-setting information including information about position of a desired area on the specimen and information about conditions under which the desired area is imaged;

means for storing said operation-setting information in memory as information records;

means for analyzing said desired area on the specimen by detecting X-rays from the desired area to thereby obtain data and storing said data as X-ray analysis data records in memory; and means for recording said information records and said X-ray analysis data records hierarchically while placing the information records at a higher level of hierarchy.

8. The data management system of claim 7, wherein said X-ray analysis data records incorporate analytical conditions corresponding to the data obtained by the analysis.

9. The data management system of claim 7 or 8, further including: means for imaging the desired area on the specimen to thereby obtain an image and storing data about the obtained image in memory as image data records; and means for recording said information records and said image data records hierarchically while placing the information records at a higher level of hierarchy.

10. The data management system of claim 9, wherein said X-ray analysis data records and said image data records are recorded at the same level of hierarchy.

11. The data management system of claim 7 or 8, further including: means for obtaining additional data about said desired area on the specimen and recording the obtained additional data as additional data records; and means for recording said information records and said additional data records hierarchically while placing the information records at a higher level of hierarchy.

12. The data management system of claim 11, wherein at least one kind of said X-ray analysis data records and said image data records is recorded at the same level of hierarchy as said additional data records.

* * * * *